(12) United States Patent
Tanaka et al.

(10) Patent No.: US 11,884,973 B2
(45) Date of Patent: Jan. 30, 2024

(54) PCR MEASURING METHOD AND MEASUREMENT DEVICE

(71) Applicant: HITACHI, LTD., Tokyo (JP)

(72) Inventors: Junko Tanaka, Tokyo (JP); Takahide Yokoi, Tokyo (JP); Masao Kamahori, Tokyo (JP); Yoshinobu Kohara, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 170 days.

(21) Appl. No.: 16/476,256

(22) PCT Filed: Nov. 16, 2017

(86) PCT No.: PCT/JP2017/041290
§ 371 (c)(1),
(2) Date: Jul. 5, 2019

(87) PCT Pub. No.: WO2018/128013
PCT Pub. Date: Jul. 12, 2018

(65) Prior Publication Data
US 2019/0352699 A1 Nov. 21, 2019

(30) Foreign Application Priority Data

Jan. 5, 2017 (JP) .................................. 2017-000772

(51) Int. Cl.
*C12Q 1/686* (2018.01)
*C12Q 1/6848* (2018.01)

(52) U.S. Cl.
CPC ........... *C12Q 1/686* (2013.01); *C12Q 1/6848* (2013.01)

(58) Field of Classification Search
CPC ........ C12Q 2531/113; C12Q 2563/107; C12Q 2563/159; C12Q 1/686
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,800,159 A | 1/1989 | Mullis et al. | |
| 2013/0017544 A1* | 1/2013 | Eckhardt | G01N 25/04 435/6.12 |
| 2016/0040219 A1* | 2/2016 | Johnson | C12Q 1/6818 435/6.11 |
| 2016/0310949 A1* | 10/2016 | Kwang | B01L 3/50273 |
| 2017/0088879 A1* | 3/2017 | Keys | C12Q 1/6851 |

FOREIGN PATENT DOCUMENTS

| | | |
|---|---|---|
| JP | 2005-229839 A | 9/2005 |
| JP | T2013-521764 A | 6/2013 |
| JP | 2016-36304 A | 3/2016 |

OTHER PUBLICATIONS

Shin, D.J. et al., A droplet microfluidic approach to single-stream nucleic acid isolation and mutation detection, Microfluid. Nanofluid., vol. 17, pp. 425-430 (Year: 2014).*
Wagner, O. et al., Biocompatible fluorinated polyglycerols for droplet microfluidics as an alternative to PEG-based copolymer surfactants, Lab on a Chip, vol. 16, pp. 65-69 (Year: 2016).*
Arya, M. et al., Basic principles of real-time quantitative PCR, Expert. Rev. Mol. Diagn., vol. 5, pp. 1-11 (Year: 2005).*
Huang, Q. et al., Multiplex Fluorescence Melting Curve Analysis for Mutation Detection with Dual-Labeled, Self-Quenched Probes, Plos One, vol. 6:4, e19206, pp. 1-9 (Year: 2011).*
Bonnet, G. et al., Thermodynamic basis of the enhanced specificity of structured DNA probes, PNAS USA vol. 96, pp. 6171-6176 (Year: 1999).*
Attali, D. et al., ddpcr: an R package and web application for analysis of droplet digital PCR data [version 1; referees 2 approved, F1000Research, vol. 5:1411, pp. 1-11 (Year: 2016).*
Rodiger, S. et al., Surface melting curve analysis with R, The R Journal, vol. 5/2, pp. 37-52 (Year: 2013).*
Huang, Q. et al., Multiplex Fluorescence Melting Curve Analysis for Muttation Detection with Dual-Labeled, Self-Quenched Probes, Plos One, vol. 6:4, e19206, supplemental Table S4 (Year: 2011).*
Huang, Q. et al., Multiplex Fluorescence Melting Curve Analysis for Muttation Detection with Dual-Labeled, Self-Quenched Probes, Plos One, vol. 6:4, e19206, supplemental Table S5 (Year: 2011).*
Huang, Q. et al., Multiplex Fluorescence Melting Curve Analysis for Muttation Detection with Dual-Labeled, Self-Quenched Probes, Plos One, vol. 6:4, e19206, supplemental Table S6 (Year: 2011).*
Vogelstein, B. et al., Digital PCR, PNAS USA, vol. 96, pp. 9236-9241 (Year: 1999).*
Zou, H. et al., High Detection Rates of Colorectal Neoplasia by Stool DNA Testing With a Novel Digital Melt Curve Assay, Gastroenterol., vol. 136, pp. 459-470 (Year: 2009).*
Rajeevan, H. et al., ALFRED: An Allele Frequency Database for Microevolutionary Studies, Evolutionary Bioinformatics Online, vol. 1, pp. 1-10 (Year: 2005).*
QX200 Droplet Digital PCR & AutoDG, Bio-Rad Laboratories, Inc.; English translation provided, 36 pages.
McDermott, G. et al., "Multiplexed Target Detection Using DNA-Binding Dye Chemistry in Droplet Digital PCR" Analytical Chemistry, 2013, vol. 85, p. 11619-11627 (9 pages).

(Continued)

*Primary Examiner* — Teresa E Strzelecka
(74) *Attorney, Agent, or Firm* — Procopio, Cory, Hargreaves & Savitch LLP

(57) ABSTRACT

The present invention is directed to provide new PCR measuring method and device. As one embodiment of the present invention, a DNA detection method for detecting DNA in a droplet being present in oil, the droplet containing the DNA and a fluorescent labeled probe, the fluorescent labeled probe being hybridized to the DNA, the method including: a first step of amplifying the DNA in the droplet by a nucleic acid amplification reaction; and a second step of measuring a melting temperature of the fluorescent labeled probe and the DNA in the droplet is provided.

10 Claims, 11 Drawing Sheets

(56) References Cited

OTHER PUBLICATIONS

Yokota, H. et al., Establishment of a Pharmacogenomic Testing System for the Realization of Individual Pharmacotherapy Medical Online, 2008, vol. 56, pp. 772-780; English abstract provided. (9 pages).

Heid, C. et al. "Real Time Quantitative PCR" Genome Research, 1996, pp. 986-994 (10 pages).

Shin et al., "A droplet microfluidic approach to single-stream nucleic acid isolation and mutation detection" Microfluid (2014) 17(2):425-430.

\* cited by examiner

FIG. 1
(A) 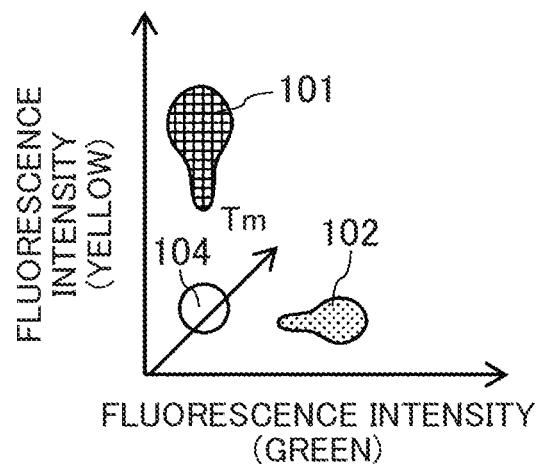
(B) 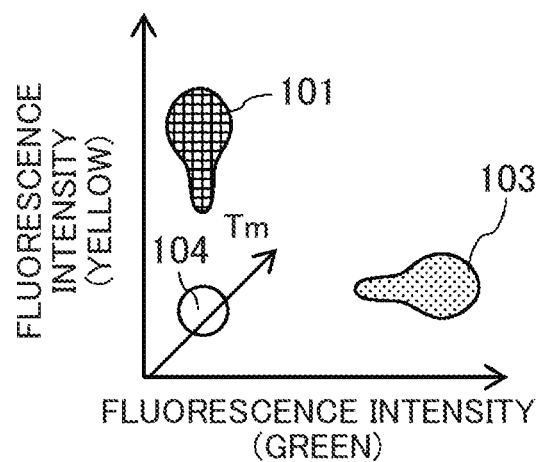
(C) 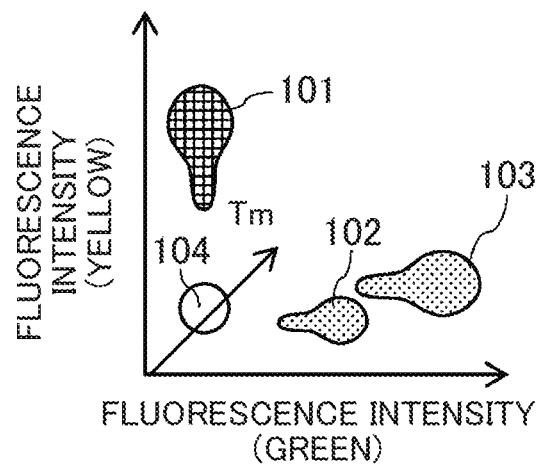

FIG. 6
(A)
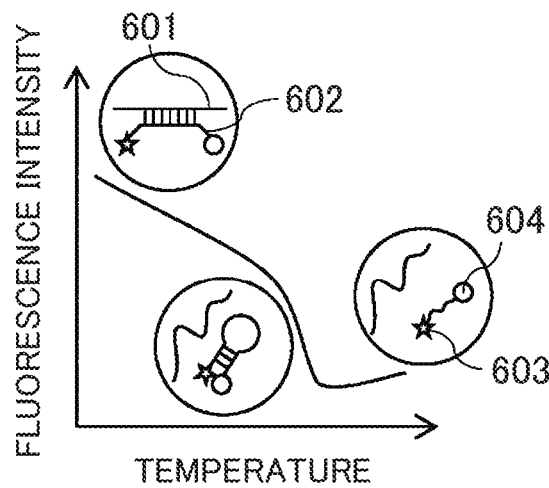
(D)
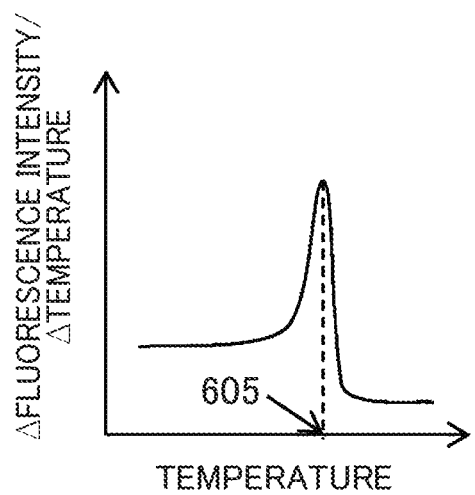
(B)
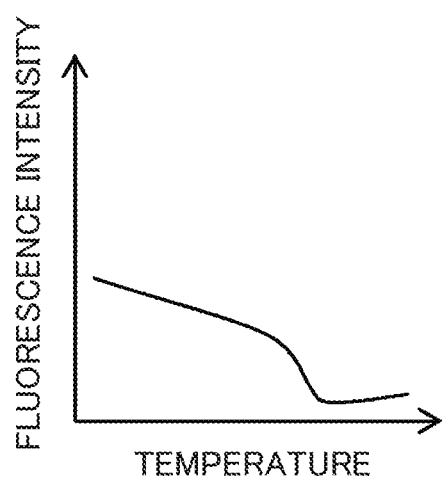
(E)
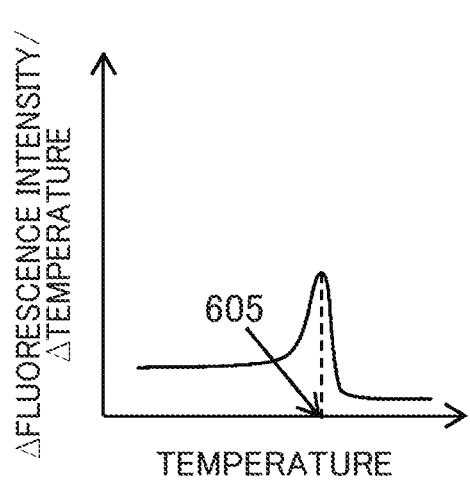
(C)
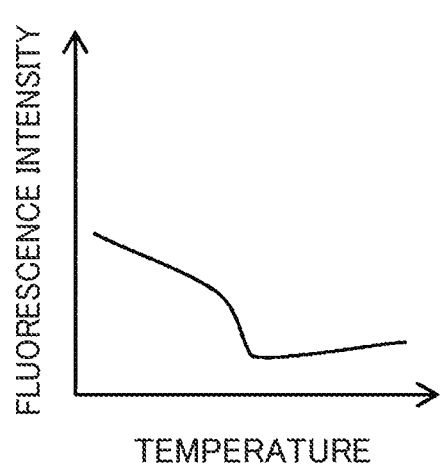
(F)
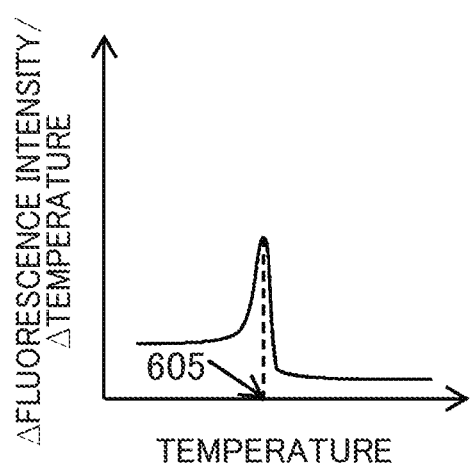

FIG. 7
(A)
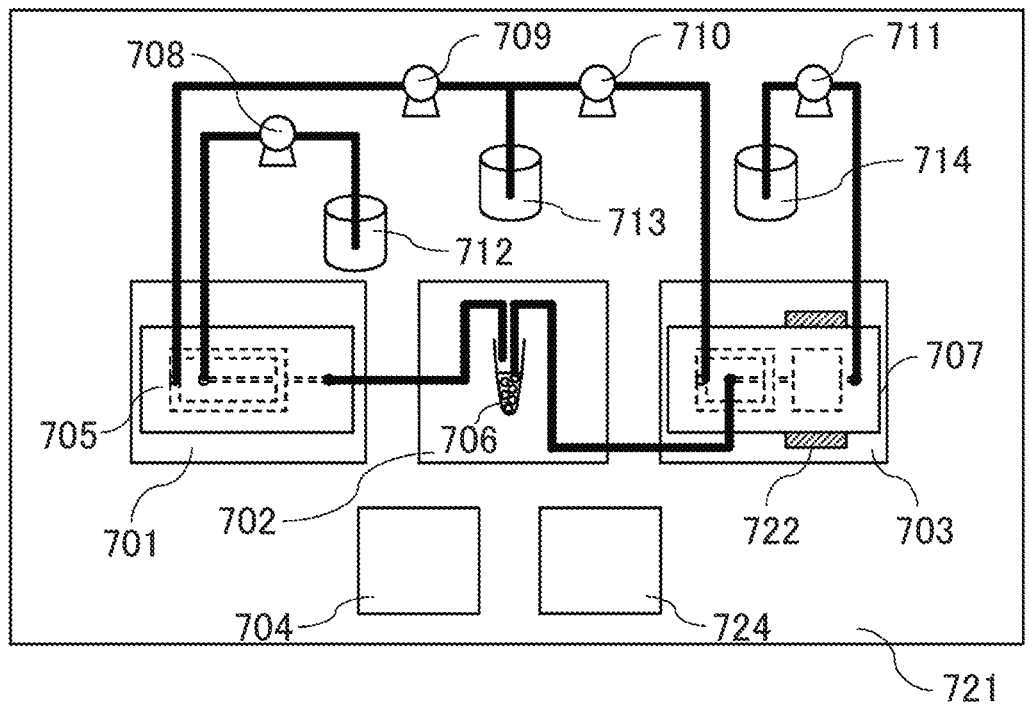
(B)
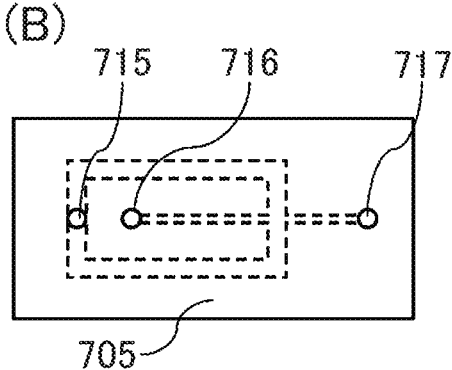
(C)
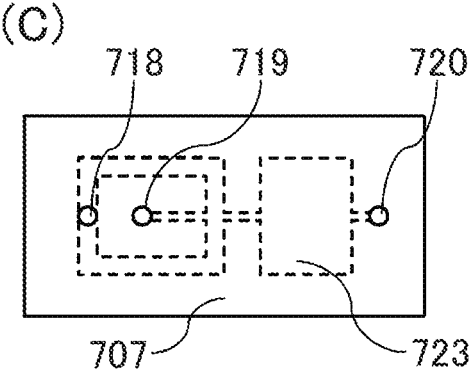

FIG. 10

| GENE | TYPE OF MUTATION | NUMBER OF DROPLETS |
|---|---|---|
| CANCER-RELATED GENE A | WILD-TYPE | 2000 |
| CANCER-RELATED GENE A | MUTANT a | 20 |
| CANCER-RELATED GENE A | MUTANT b | 100 |
| EMPTY | | $5 \times 10^6$ |

FIG. 11

| GENE | TYPE OF MUTATION | PERCENTAGE (%) |
|---|---|---|
| CANCER-RELATED GENE A | WILD-TYPE | 94 |
| CANCER-RELATED GENE A | MUTANT a | 0.1 |
| CANCER-RELATED GENE A | MUTANT b | 5 |
| CANCER-RELATED GENE B | WILD-TYPE | 80 |
| CANCER-RELATED GENE B | MUTANT c | 10 |
| CANCER-RELATED GENE B | MUTANT d | 10 |

FIG. 12
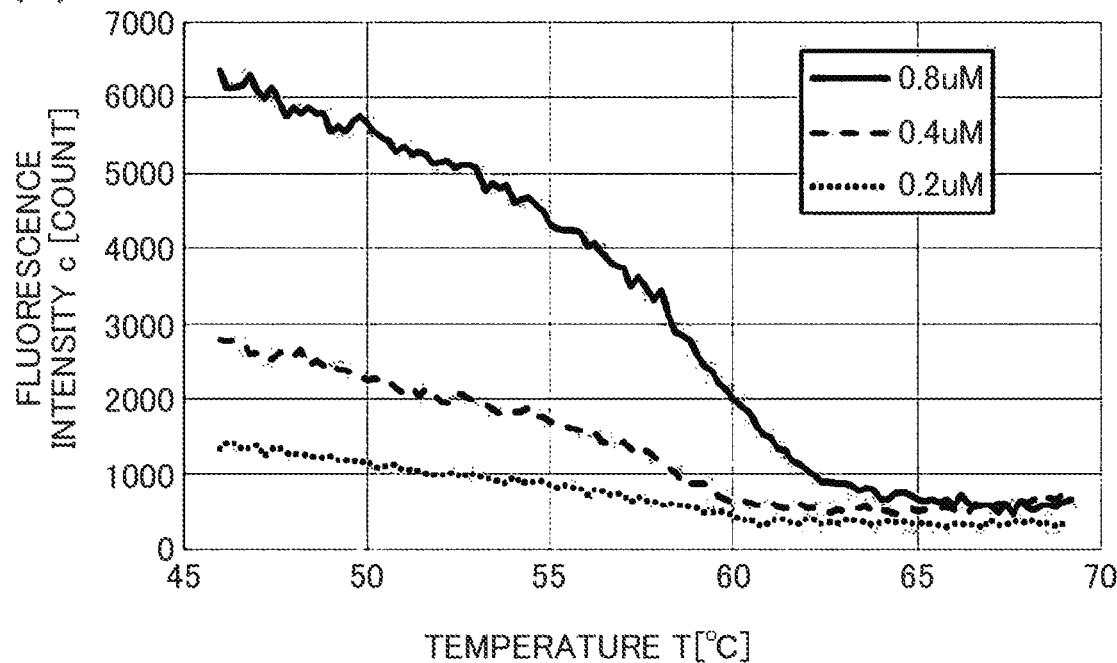
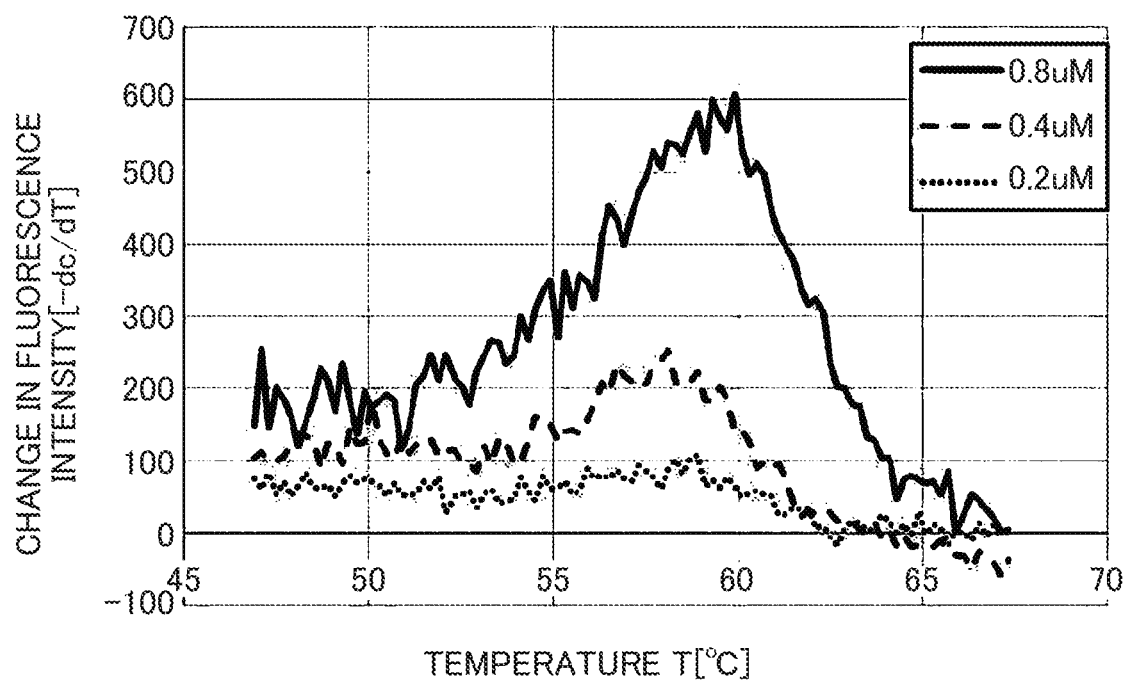

PCR MEASURING METHOD AND MEASUREMENT DEVICE

CROSS-REFERENCE TO RELATED APPLICATIONS

This application is a U.S. National Stage entry of PCT Application No: PCT/JP2017/041290 filed on Nov. 16, 2017, which claims priority to Japanese Patent Application No. 2017-000772, filed on Jan. 5, 2017, which is hereby incorporated by reference.

TECHNICAL FIELD

The present invention relates to PCR measuring methods and measurement devices.

BACKGROUND ART

In diagnoses of cancers and infectious diseases, quantification of cancer-related genes and virus-derived genes which are contained in very small amounts in a sample and detection of mutations which exist in a very small amount in comparison with the total amount of target cancer-related genes are required. In such a genetic test, PCR (U.S. Pat. Nos. 4,683,195, 4,683,202, and 4,800,159) or real-time PCR (Genome Res., 10, pp 986-994, 1996) has been used so far. The PCR is a semi-quantitative analytical technique of detecting an amplified target gene at its endpoint by agarose electrophoresis. On the other hand, the real-time PCR is a quantitative analytical technique of detecting a process, in which the target gene is exponentially amplified, by using a fluorescent labelled probe, a DNA intercalator and so forth in real time.

In recent years, opportunities in which a more highly sensitive genetic test is required have been increased because of a reduction in sample amount or for early diagnoses and the importance of being able to make reproducible and quantitative measurement in such a highly sensitive genetic test has been increased. Although quantitative measurement of the target gene is possible in the real-time PCR, it has been a problem that reproducibility in the quantitative measurement is lower when the amount of target genes is very small. This is caused because in the real-time PCR, a calibration curve made by using a target gene which has been adjusted to a known concentration as a sample is needed for measurement and therefore absolute quantification is not possible and amplification efficiency of the PCR depends on a sample-derived component.

Droplet Digital PCR® (JP-T-2013-521764) was developed as a method of solving the problem that measurement reproducibility is lower when the amount of target genes is very small in conventional genetic tests by performing absolute quantification using a limitingly diluted sample. An experimental procedure of the Droplet Digital PCR will be described in the following. First, DNA polymerase, primers, a fluorescent labeled probe, which are necessary for the PCR, are added to a limitingly diluted sample and droplets of a PCR solution are prepared in oil. One or zero molecules of a target gene are contained in one droplet of the prepared droplets. Next, the target gene in the droplet is amplified by the PCR. Fluorescence intensity of each droplet is measured after the PCR, and by counting the number of the droplets having fluorescence intensities which exceed a threshold value, the target genes are quantified. In the Droplet Digital PCR, an influence of the sample-derived component which becomes an inhibitory factor of the PCR is suppressed by using the limitingly diluted sample. In addition, a calibration curve is not needed and therefore the absolute quantification becomes possible.

In the PCR, it is known that the reaction efficiency is reduced due to presence of a reaction inhibitor in the reaction solution, formation of a secondary structure of template DNA, insufficiency in design of the primers and so forth. It has been thought so far that since measurement is performed at the endpoint, the reaction efficiency of the PCR does not largely affect the result of measurement in the Droplet Digital PCR. However actually in a case that the PCR of 40 cycles is performed with a droplet which contains one molecule of DNA, the number of molecules in the PCR amplification product greatly differs depending on the reaction efficiency of one cycle. For example, when the reaction efficiency of one cycle is two times, it is amplified to $1.1 \times 10^{12}$ molecules, when the reaction efficiency of one cycle is 1.5 times, it is amplified to $1.1 \times 10^{7}$ molecules, when the reaction efficiency of one cycle is 1.4 times, it is amplified to $0.7 \times 10^{6}$ molecules. In a case that the size of the droplet is 4 pL and it contains 1-µM primers, the number of molecules of the primers is $2.4 \times 10^{6}$ molecules and when the reaction efficiency of one cycle is 1.5 or more times, the number of molecules of the PCR amplification product is restricted depending on the concentration of the primer. However, when the reaction efficiency of one cycle is not more than 1.4 times, the number of molecules of the PCR amplification product greatly differs depending on the reaction efficiency of one cycle. Accordingly, when the reaction efficiencies of the individual droplets are not equalized, a variation in droplet fluorescence intensity increases.

SUMMARY OF INVENTION

Technical Problem

An object of the present invention is to provide a new PCR measuring method and a measurement device of the PCR using droplets.

SUMMARY OF THE INVENTION

The inventors of the present invention found that the measurement reproducibility and measurement accuracy can be improved by measuring a melting temperature (Tm) of the PCR amplification product in addition to the color and the fluorescence intensity of the fluorescent labeled probe and reached completion of the present invention.

An aspect of the present invention is a DNA detection method for detecting DNA in each of one or more droplets being present in oil, each droplet containing the DNA and a fluorescent labeled probe, the fluorescent labeled probe being hybridized to the DNA, the method including: a first step of amplifying the DNA in the one or more droplets by a nucleic acid amplification reaction; and a second step of measuring a melting temperature of the fluorescent labeled probe and the DNA in the one or more droplets. The fluorescent labeled probe contains a fluorescent dye and a quencher thereof, and the melting temperature of the fluorescent labeled probe and the DNA may be measured based on change in fluorescence intensity of the fluorescent dye in association with temperature increase of the one or more droplets.

Another aspect of the present invention is a DNA detection method for detecting DNA in each of one or more droplets being present in oil, each droplet containing the DNA and a DNA intercalator, the method including: a first step of amplifying the DNA in the one or more droplets by a nucleic acid amplification reaction; a second step of measuring an intensity of fluorescence emitted from the DNA intercalator upon temperature increase of the one or more droplets; and a third step of calculating a melting temperature of a double-strand of the DNA based on change in the intensity of fluorescence in association with temperature increase of the one or more droplets.

In the DNA detection method according to any one of the above, a plurality of the droplets may be planarly disposed. Furthermore, the oil may contain a fluorine-based oil, a silicone-based oil, or a hydrocarbon-based oil.

A yet another aspect of the present invention is a DNA determination method for determining whether or not a certain DNA is contained in a droplet in oil, the droplet containing a fluorescent labeled probe, the fluorescent labeled probe being hybridized to the DNA, the method including: a first step of performing a nucleic acid amplification reaction in the droplet; and a second step of measuring a melting temperature of the fluorescent labeled probe and the DNA in the droplet, wherein when an amplification product cannot be detected in the first step and/or when the melting temperature is out of a predetermined range in the second step, it is determined that the DNA is not contained in the droplet.

A yet another aspect of the present invention is a DNA determination method for determining whether or not a certain DNA is contained in a droplet in oil, the droplet containing an DNA intercalator, the method including: a first step of performing a nucleic acid amplification reaction in the droplet; a second step of measuring an intensity of fluorescence emitted from the DNA intercalator upon temperature increase of the droplet; and a third step of calculating a melting temperature of a double-strand of the DNA based on change in the intensity of fluorescence in association with temperature increase of the droplet, wherein when an amplification product cannot be detected in the first step and/or when the melting temperature is out of a predetermined range in the third step, it is determined that the DNA is not contained in the droplet.

In the determination method according to any one of the above, it may be determined that the DNA is contained in the droplet when the amplification product can be detected, and the melting temperature is within the predetermined range.

A still another aspect of the present invention is a DNA detection device for detecting DNA in a droplet in oil, the device including: a heating unit for heating the droplet in the oil; a fluorescence measurement unit for measuring intensity of fluorescence from a fluorescent labeled probe or a DNA intercalator in the oil; and a calculation unit for calculating a melting temperature of the fluorescent labeled probe and the DNA or a melting temperature of a double-strand of the DNA from change in the intensity of fluorescence in association with temperature increase of the droplet. The device may further include an amplification unit for amplifying DNA in the droplet in the oil. The device may include a monitor on which the presence or absence of DNA in the droplet is displayed.

A further aspect of the present invention is a program for causing a DNA detection device to perform the DNA detection method according to any one of the above or the DNA determination method according to any one of the above. This DNA detection device may be the aforementioned DNA detection device.

BRIEF DESCRIPTION OF DRAWINGS

FIGS. 1(A)-1(C) show diagrams illustrating a basic concept in one embodiment of the present invention;

FIGS. 6(A)-6(F) show schematic diagrams illustrating a method of measuring Tm of DNA using a fluorescent labeled probe in one embodiment of the present invention;

FIGS. 7(A)-7(C) show schematic diagrams illustrating a device for performing a DNA detection method and cartridges to be used in the device in one embodiment of the present invention;

FIG. 10 shows one example of a measurement result displayed on a monitor;

FIG. 11 shows one example of a measurement result displayed on the monitor; and

FIGS. 12(A)-12(B) show graphs illustrating results of measurement of Tm of DNA which has been amplified in a droplet using a DNA intercalator in one embodiment of the present invention.

DESCRIPTION OF EMBODIMENTS

Objects, characteristics, advantages, and ideas of the present invention are apparent to a person skilled in the art from the description of the present specification and the person skilled in the art can easily reproduce the present invention from the description of the present specification. Embodiments of the present invention, specific examples thereof and so forth, which are described in the following, indicate preferable embodiments of the present invention and are described for exemplification or explanation, and the present invention is not limited thereto. It is apparent to the person skilled in the art that various alterations and modifications can be made on the basis of the description of the present specification within the intention and the scope of the present invention disclosed in the present specification.

(1) Principle and Effects of DNA Detection Method

A DNA detection method according to the present invention includes, in a droplet which is present in oil and contains DNA and a fluorescent labeled probe which is hybridized to the DNA, a step of amplifying the DNA in the droplet by a nucleic acid amplification reaction and a step of measuring melting temperatures of the fluorescent labeled probe and the DNA or the double-stranded DNA by a melting curve analysis.

Figure 2:
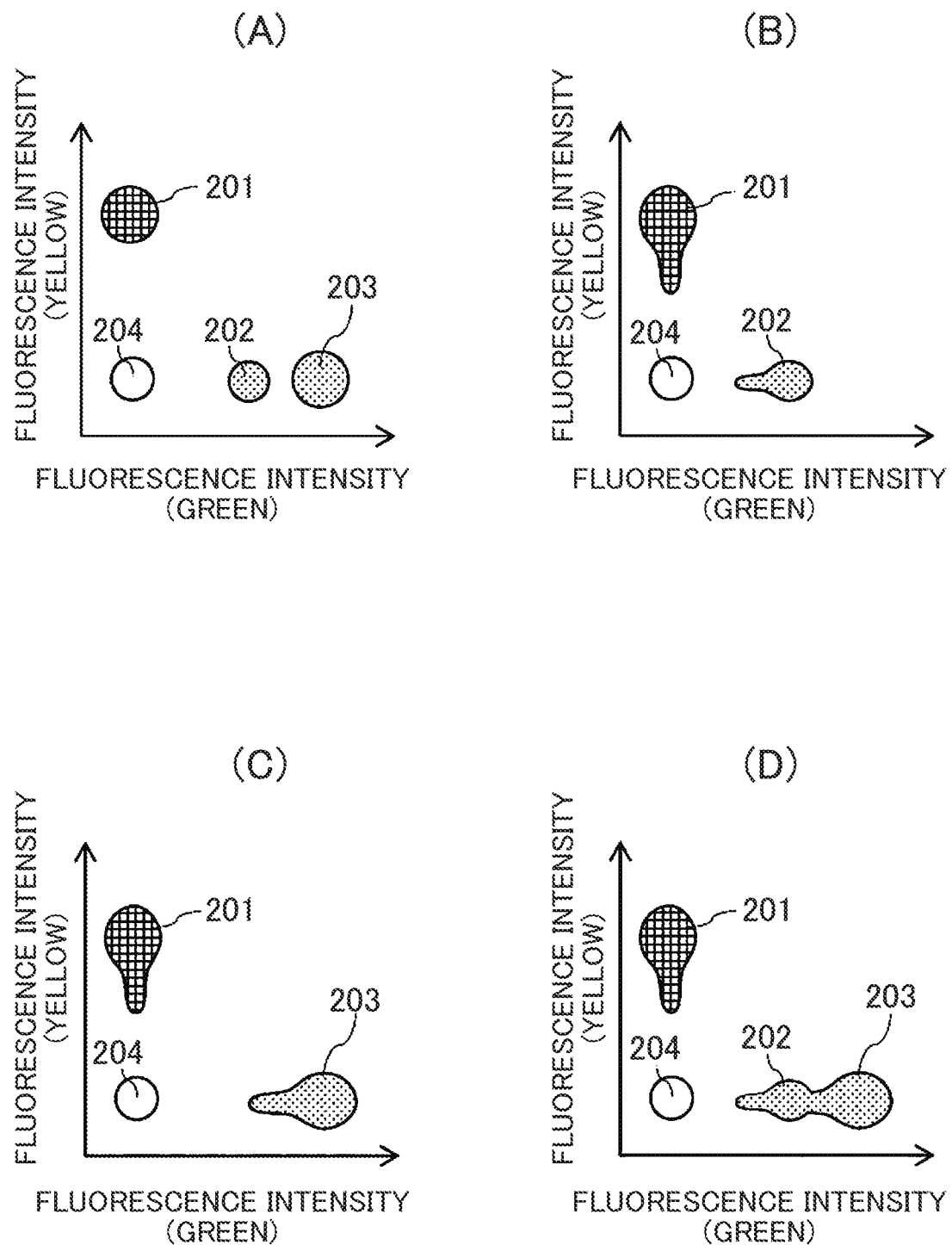
FIGS. 2(A)-2(D) show diagrams illustrating examples of results of measurement of conventional Droplet Digital PCR.

Examples of measurement results which are assumed in a representative embodiment of the present invention are illustrated in FIG. 1. In addition, examples of multiplex measurement results in conventional Droplet Digital PCR are illustrated in FIG. 2.

In the Droplet Digital PCR, multiplex PCR may be performed, in which a plurality of kinds of mutations of the DNA are detected in a single measurement by using different colors and different amounts of the fluorescent labeled probes depending on the mutations. In an example in FIG. 2A, shown is a diagram schematically illustrating a result in the case that a yellow fluorescent labeled probe is used for a wild-type allele of a target gene, a green fluorescent labeled probe is used for a mutant allele of the target gene and they are used such that the ratio of the amount of the fluorescent labeled probes for a mutation A and the amount thereof for a mutation B of the target gene is 3:5. In this example, the fluorescent labeled probe is configured to be complementary to a sequence between a primer pair used in the PCR and to be degraded when the primer is extended so that a fluorescent label emits fluorescence. Specifically, a TaqMan® probe can be exemplified. In a droplet 201 which contains the target gene with the wild-type allele, the yellow fluorescent labeled probe which corresponds to the wild-type allele of the target gene is degraded simultaneously with amplification of the DNA during the PCR and emits yellow fluorescence. In addition, in a droplet 202 which contains the target gene with the mutant A allele, the green fluorescent labeled probe which corresponds to the mutant A allele of the target gene is degraded simultaneously with amplification of the DNA during the PCR and emits green fluorescence. In a droplet 203 which contains the target gene with the mutant B allele, the green fluorescent labeled probe which corresponds to the mutant B of the target gene is degraded simultaneously with amplification of the DNA during the PCR and emits green fluorescence. On this occasion, the ratio of the fluorescence intensity of the droplet which contains the mutant A allele and the green florescence intensity of the droplet which contains the mutant B allele is 3:5 in proportion to the amounts of the fluorescent labeled probes which have been added to the droplets. In an empty droplet 204 which does not contain the target gene, neither of the green fluorescence and the yellow fluorescence are detected. However, since there actually exist droplets in which the PCR reactions are insufficient as shown in FIGS. 2B and 2C, a distribution of the fluorescence intensities of the droplets may be widened. In addition, when an expansion of the fluorescence intensity distribution becomes too large, the distributions of the mutant A droplet 202 and the mutant B droplet 203 may overlap each other as shown in FIG. 2D.

In addition, as shown in FIG. 2A, in the Droplet Digital PCR, since the droplets are prepared by limitingly diluting a sample so as to put one or zero molecules of a target gene into one droplet, 50 to 90% of the prepared droplets become empty droplets 204 which do not contain the target gene. Even in such an empty droplet, some fluorescent labeled probes may be degraded due to a sample-derived component so that the fluorescent dye and a quencher thereof may be cut apart and it may emit fluorescence; therefore, such empty droplets are excluded by setting a threshold value. In addition, in the Droplet Digital PCR, multiplex PCR in which a plurality of kinds of mutations are detected in a single measurement is realized by using different colors and different amounts of the fluorescent labeled probes depending on the mutations; therefore, the threshold value is set from the color and the intensity of the fluorescent dye after the PCR, and the numbers of the droplets 201, 202, 203 which contain the target gene are counted.

In an experiment of the Droplet Digital PCR, an experimenter has set the threshold value by which the aforementioned empty droplets which do not contain the target gene are excluded from data and the number of the droplets is counted for each kind of mutations after the multiplex PCR. However, a large dispersion of fluorescence intensities of the droplets makes threshold value setting difficult and becomes a cause of low measurement accuracy.

In one embodiment of the present invention, as described above, the step of calculating the melting temperature Tm of the fluorescent labeled probe and the DNA or the melting temperature Tm of the double-stranded DNA is included. This step makes it possible to plot a result of measurement of the droplets with three axes of the green fluorescence intensity, the yellow fluorescence intensity and Tm as shown in FIG. 1 so that droplet groups 101 to 104 are mutually separated.

In addition, empty droplets which do not contain the target gene and droplets in which the reaction efficiency of the PCR is insufficient can be certainly discriminated with a measurement device and the measurement reproducibility and the measurement accuracy can be improved by adjusting data of the target to be analyzed.

(2) DNA Detection Device

Figure 3:
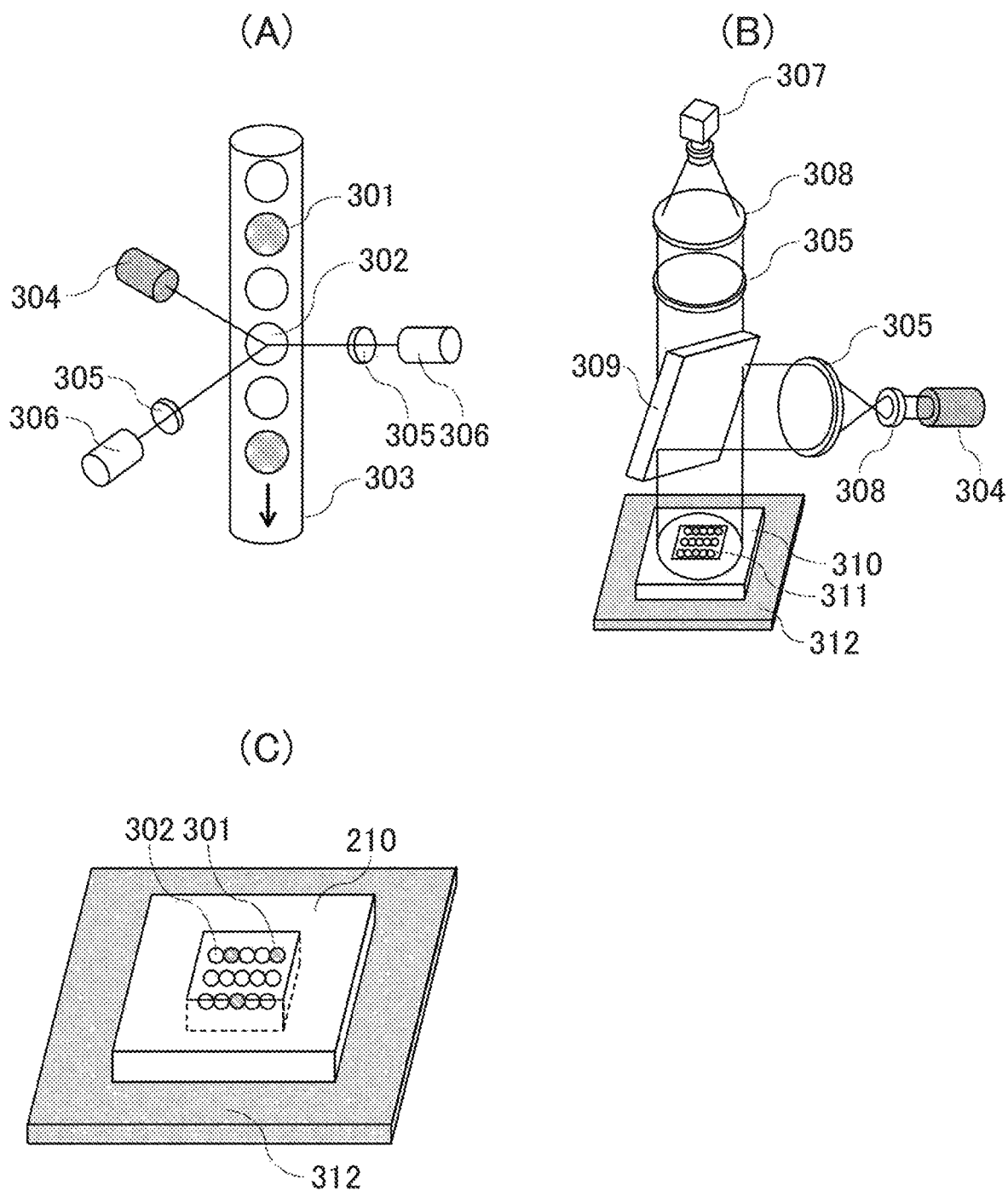
FIGS. 3(A)-3(C) show schematic diagrams of fluorescence measurement units for measuring colors and fluorescence intensities of fluorescent dyes in a droplet in one embodiment of the present invention.

A DNA detection device of the present invention is equipped with a heating unit for heating droplets in oil, a fluorescence measurement unit for measuring intensity of fluorescence from a fluorescent labeled probe in the oil or a DNA intercalator, and a calculation unit for calculating the melting temperature of the fluorescent labeled probe and the DNA or the melting temperature of the double-stranded DNA from change in fluorescence intensity in association with temperature increase of the droplet. FIG. 3 shows an example of the fluorescence measurement unit for measuring color and fluorescence intensity of a fluorescent dye contained in the droplet.

In the example of the fluorescence measurement unit which is shown in FIG. 3A, the fluorescence intensity of each droplet is measured using a microchannel. Droplets 301 flow through a microchannel 303 in the direction of an arrow. When a droplet flows to a position where a droplet 302 is illustrated, it is irradiated with excitation light from a light source 304 while the droplet is being heated by the heating unit (not shown). A fluorescent substance contained in the droplet is excited with the light source 304 and fluorescence that the fluorescent substance emits is detected by a photo-multiple meter 306 through a fluorescence filter 305. Data on the detected fluorescence is sent to the calculation unit (not shown) and there the melting temperature of the fluorescent labeled probe and the DNA or the melting temperature of the double-stranded DNA is detected. A fluorescence detector which is configured with the light source 304, the fluorescence filter 305, the photo-multiple meter 306 may be independently provided for each fluorescent dye color or may be configured to excite the fluorescent substance with excitation light from one light source and simultaneously detect each of the fluorescences with two fluorescence filters as shown in FIG. 3A.

In addition, as shown in FIGS. 3B and 3C, droplets may be planarly disposed and the colors and the fluorescence intensities of the fluorescent dyes of the droplets may be measured. Specifically, for example, droplets 311 are planarly disposed on a cartridge for droplet detection 310 and the cartridge is set on a temperature regulation stage 312 which is the heating unit. The temperature of the cartridge for droplet detection is changed with a temperature regulator 312, and the fluorescence intensities of the droplets, which are associated with the temperature change, are measured in the following procedures. First, the droplets 311 which are planarly disposed on the cartridge for droplet detection 310 are irradiated with excitation light from the light source 304 through a lens 308, a filter 305 and a dichroic mirror 309. The fluorescent substance contained in the droplets is excited with the excitation light and the fluorescence which is emitted therefrom is detected with a CCD camera 307 through the dichroic mirror 309, the filter 305, and the lens 308. Data on the detected fluorescence is sent to the calculation unit (not shown) and a melting temperature of an amplification product is calculated there. Although in FIG. 3A, it is necessary to process the droplets one by one, the device in FIGS. 3B and 3C is preferable in that many droplets can be processed all at once. In addition, the device in FIGS. 3B and 3C is preferable to that in FIG. 3A also in that the temperature regulator 312 can be used also for an amplification reaction of the DNA.

(3) Method of Calculating Melting Temperature

Figure 4:
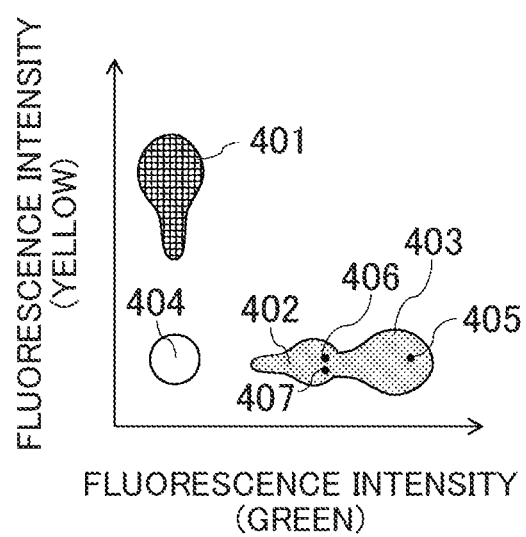
FIG. 4 shows a diagram illustrating one example of a result of measurement by the conventional Droplet Digital PRC, in which a gene contained in a droplet cannot be identified.
Figure 5:
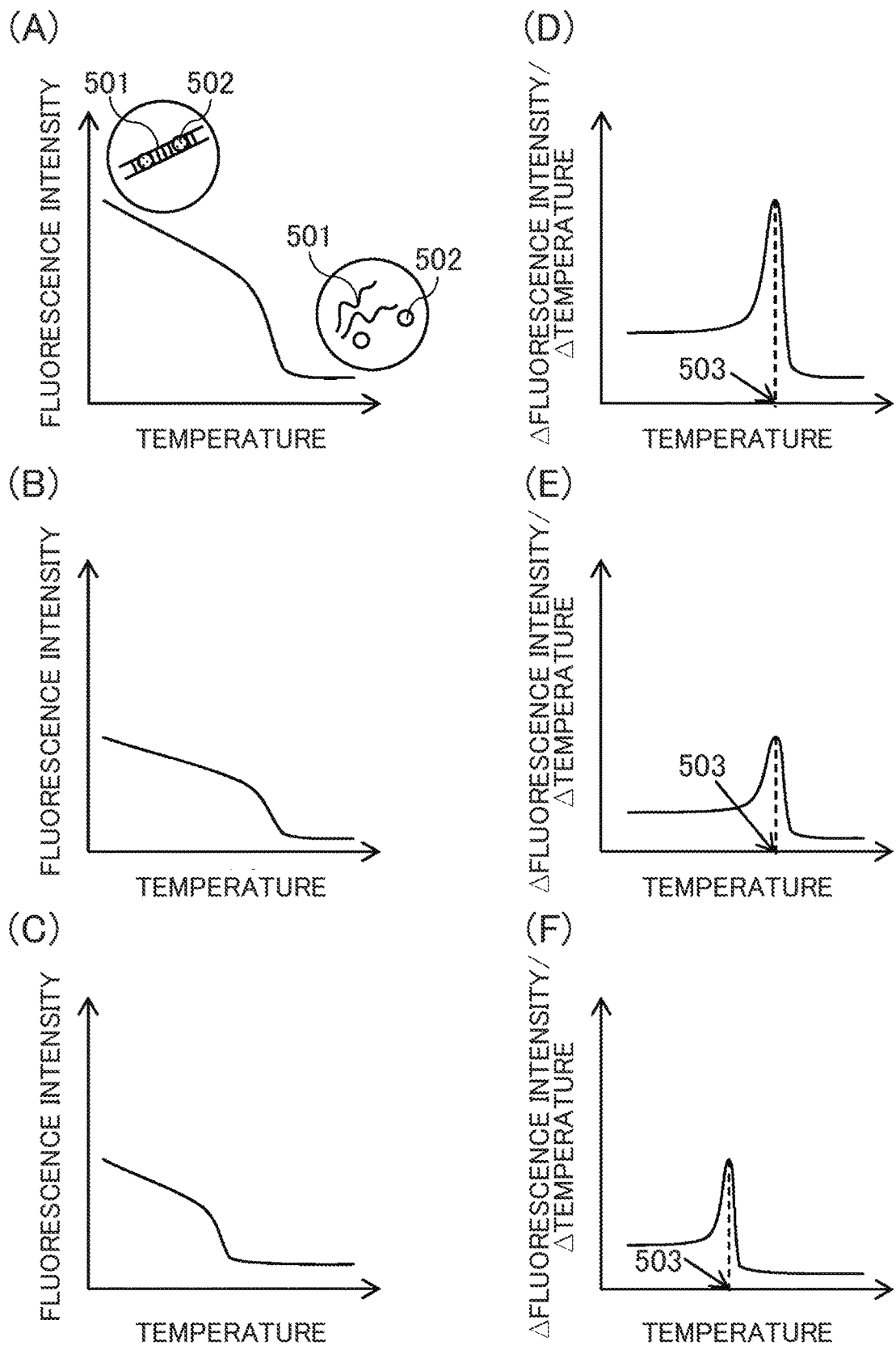
FIGS. 5(A)-5(F) show schematic diagrams illustrating a method of measuring Tm of DNA using a DNA intercalator in one embodiment of the present invention.

FIG. 4 is one example of a schematic diagram showing a measurement result in which the detected fluorescence intensities overlap each other in a similar way to FIG. 2D so that the gene which is contained in droplets cannot be identified. FIGS. 5 and 6 are examples of schematic diagrams showing results of measurement of Tm of the DNA which has been amplified in the droplets for the target gene which could not be identified in FIG. 4.

As shown in FIG. 4, in a case of the multiplex PCR that the plurality of kinds of mutations are detected in a single measurement by using different colors and different amounts of the fluorescent labeled probes depending on each mutation, since both a mutant A 402 and a mutant B 403 of the target gene are detected using the green fluorescent labeled probe, it can be understood that the target gene that the droplet contains is the mutant B when fluorescence intensity of the droplet a 405 is observed. However, when fluorescence intensities of the droplet b 406 and the droplet c 407 are observed, it cannot be decided from the measurement result which the target gene that the droplet contains is, the mutant A 402 or the mutant B 403.

Considering the above, as shown in FIGS. 5, the target gene whose mutation could not be identified in FIG. 4 can be identified by measuring Tm of the DNA which has been amplified in droplets using a DNA intercalator. Specifically, first, when droplets are prepared by adding a DNA intercalator 502 to a PCR reaction solution and a nucleic acid amplification reaction such as PCR is conducted, the DNA intercalator 502 is bound to double-stranded DNA 501 amplified in the droplets at a temperature around room temperature and the intercalator emits strong fluorescence. Then, as the temperature of the droplets is increased, the double-stranded DNA 501 in the droplets dissociates and becomes single-stranded DNA 501 and the DNA intercalator 502 ceases to bind thereto and therefore the fluorescence intensity decreases. One example of results obtained when plotting changes in fluorescence intensity relative to changes in temperature on a graph is illustrated in FIG. 5. It should be noted that changes in fluorescence intensity relative to changes in temperature may be measured also by increasing the temperature of the droplet independently of the nucleic acid amplification reaction (e.g., after completion of the nucleic acid amplification reaction).

FIGS. 5A, 5B, and 5C show measurement results for the droplets a 405, b 406, and c 407, respectively. Furthermore, differentiations of the changes in fluorescence intensity with respect to the changes in temperature shown in FIG. 5A to 5C yield the results as shown in FIG. 5D to 5F, respectively.

Thus, temperatures at the inflection points of the curves showing the changes in fluorescence intensity can be obtained as calculation results for the melting temperatures Tm of the double-stranded DNA. In FIG. 4, it cannot be determined, from the measurement result, which the target genes that the droplets b 406 and c 407 contain belong to, a group 402 of the mutant A droplets or a group 403 of the mutant B droplets. In contrast, it can be determined that the droplet b 406 contains the mutant B because Tm of the droplet b 406 is the same as that of the droplet a 405 as shown in FIGS. 5D and 5E while the droplet c 407 contains the mutant A because Tm of the droplet c 407 is different from that of the droplet a 405 as shown in FIGS. 5D and 5F. Furthermore, in the case that the target gene has any unexpected mutation other than the mutations A and B, Tm of the droplet subjected to the measurement can be detected with a value that is different from that for any of the wild-type droplet 401, the mutant A droplet 402, and the mutant B droplet 403; thus, not only expected mutations, but also unexpected ones can be detected in a single measurement.

Note that Tm of the target gene can be controlled depending on a sequence of a PCR amplification product or its length by altering the design of primers.

Any DNA intercalator can be appropriately used here as long as its fluorescence intensity increases as a result of its binding to double-stranded DNA and thus it can be used for detecting the double-stranded DNA. Specifically, for example, SYBR® Green I, SYBR Gold, PicoGreen®, SYTO® Blue, SYTO Green, SYTO Orange, SYTO Red, POPO®-1, BOBO®-1, YOYO®-1, TOTO®-1, JOJO®-1, POPO-3, LOLO®-1, BOBO-3, YOYO-3, TOTO-3, PO-Pro®-1, YO-Pro®-1, TO-Pro®-1, JO-Pro®-1, PO-Pro-3, YO-Pro-3, TO-Pro-3, TO-Pro-5, and ethidium bromide can be appropriately used. When the DNA intercalator has heat resistance, it can be added to the droplets before performing a PCR reaction.

In this method, as a substitute for the DNA intercalator, a fluorescent labeled probe can also be used. The fluorescent labeled probe is designed such that it has sequences, near both ends, which are complementary to each other and forms a stem-loop structure like a molecular beacon, with a fluorescent dye and its quencher conjugated at or in the vicinity of the respective ends while the sequence of the loop portion is complementary to that of the template DNA so that the probe can hybridize with the template DNA. When the fluorescent labeled probe 602 exists in a free form, it forms the stem-loop structure and no fluorescence emission occurs because a fluorescent dye 603 and a quencher 604 are in close proximity. When the fluorescent labeled probe 602 is added to the droplets for which PCR reaction has already been completed, the loop portion of the fluorescent labeled probe 602 anneals, at or around room temperature, to DNA 601 which has been amplified in the droplet. This causes the fluorescent dye 603 and the quencher 604 to move away from each other, and the fluorescent labeled probe 602 emits strong fluorescence. Thereafter, when the droplet is heated, the DNA 601 dissociates from the fluorescent labeled probe 602 and a stem-loop is formed in the fluorescent labeled probe 602 so that the intensity of the fluorescence emission from the fluorescent labeled probe 602 decreases. When the droplet is further heated, the stem of the stem-loop structure of the fluorescent labeled probe 602 is dissociated so that the fluorescence intensity increases again. One example of a result, when a change in fluorescence intensity relative to a change in temperature on a graph is plotted, is shown in FIG. 6. This fluorescent labeled probe may be used also as the fluorescent labeled probe for PCR at the same time, a fluorescent labeled other than the one for PCR may be made and used. In addition, change in the fluorescence intensity relative to change in the temperature may be measured during a nucleic acid amplification reaction or instead, may be measured independently from the nucleic acid amplification reaction (e.g., after the completion of the nucleic acid amplification reaction) by heating the droplet.

In FIG. 6, measurement results for the droplets a 405, b 406, and c 407 are as shown in FIGS. 6A, 6B, and 6C, respectively. Furthermore, differentiation of the changes in fluorescence intensity in FIG. 6A to 6C with respect to change in temperature results as shown in FIG. 6D to 6F, respectively; thus, temperatures at the inflection points on the fluorescence intensity curves can be obtained and serve as melting temperatures Tm of the fluorescent labeled probes and the DNAs for detecting the target genes. In FIG. 4, it cannot be determined from the measurement result which the target gene that the respective droplets b 406 and c 407 contain belong to, a group of the mutant A droplets 402 or a group of the mutant B droplets 403. In contrast, it can be determined that the droplet b 406 is the mutant B because Tm of the droplet b 406 is the same as that of the droplet a 405 as shown in FIGS. 6D and 6E while the droplet c 407 is the mutant A because Tm of the droplet c 407 is different from that of the droplet a 405 as shown in FIGS. 6D and 6F. Furthermore, even if the target gene has any unexpected mutation other than the mutations A and B, such the unexpected mutation can be detected from a single measurement result like the expected mutations, since Tm of the droplet subjected to the measurement can be detected with a value that is different from that for any of the wild-type droplet 401, the mutant A droplet 402, and the mutant B droplet 403.

Note that Tm of the fluorescent labeled probe for detecting the target gene can be controlled by altering its sequence or its length. In addition, Tm can also be controlled by using artificial DNA such as Peptide Nucleic Acid (PNA) or Locked Nucleic Acid (LNA).

Combination of the fluorescent dye 603 and the quencher 604 of the fluorescent labeled probe 602 is not limited as long as it is usually used in real-time PCR. Examples of the fluorescent dye 603 include FAM, VIC, ROX, Cy3, and Cy5 and examples of the quencher 604 include TAMRA, BHQ1, BHQ2, and BHQ3.

The sequence recognized by the fluorescent labeled probe 602 may be of the target gene or of a different gene, or may be different from the target gene by one base, such as those of a wild-type and a mutant of a gene. For example, in the case of genetic testing of lung cancer, the presence or absence of an ALK fusion gene and an EGFR gene mutation is determined in order to predict the efficacy of a molecular targeted drug. In this case, sequences which recognize each of the ALK fusion gene and the EGFR gene, or recognize each of the L858R mutant and the wild-type of EGFR may be used.

(4) Another Configuration of DNA Detection Device

A DNA detection device according to one embodiment of the present invention may include a droplet production unit for producing droplets by adding a DNA solution containing target DNA to oil and/or an amplification unit for amplifying DNA in droplets.

FIG. 7 is a diagram showing an example of a device for implementing the method of the present invention and a cartridge used in this device. As shown in FIG. 7(A), a PCR measurement device 721 is composed of a droplet production unit 701, a thermal cycler 702 as an amplification unit, a droplet detection unit 703, a monitor 704, and a control unit 724. The droplet production unit 701 is used with a cartridge 705 for droplet production shown in FIG. 7(B) loaded thereon. The cartridge 705 for droplet production has an oil supply inlet 715, a PCR solution inlet 716, and a droplet discharge outlet 717. The droplet detection unit 703 is used with a cartridge 707 for droplet detection shown in FIG. 7(C) loaded on a temperature regulator 722. The cartridge 707 for droplet detection has an oil supply inlet 718, a droplet inlet 719, a reservoir 723, and a waste liquid discharge outlet 720. The oil supply inlet 715 of the cartridge for droplet production is in fluid communication with the PCR measurement device 721 and is supplied with oil 713 by a pump 709. The PCR solution inlet 716 of the cartridge for droplet production 705 is in fluid communication with the PCR measurement device 721 and is supplied with gas such as nitrogen gas or air or with oil 712 by a pump 708. The droplet discharge outlet 717 of the cartridge for droplet production is in fluid communication with the PCR measurement device 721 and is connected to a microtube 706 mounted in the thermal cycler 702. The oil supply inlet 718 of the cartridge 707 for droplet detection is in fluid communication with the PCR measurement device 721 and is supplied with the oil 713 by a pump 710. The droplet inlet 719 of the cartridge 707 for droplet detection is in fluid communication with the PCR measurement device 721 and is connected to the microtube 706 mounted in the thermal cycler 702. The waste liquid discharge outlet 720 of the cartridge 707 for droplet detection is in fluid communication with the PCR measurement device 721 and the waste liquid in the cartridge 707 for droplet detection is discharged into a waste liquid reservoir 714 by a pump 711. Each of the pumps may be a peristaltic pump, a syringe pump, or a diaphragm pump. The monitor 704 serves as a display unit on which results of measurement and messages are displayed and also as an input unit with which a user enters his or her commands.

(5) Methods of Measuring Tm

Figure 8:
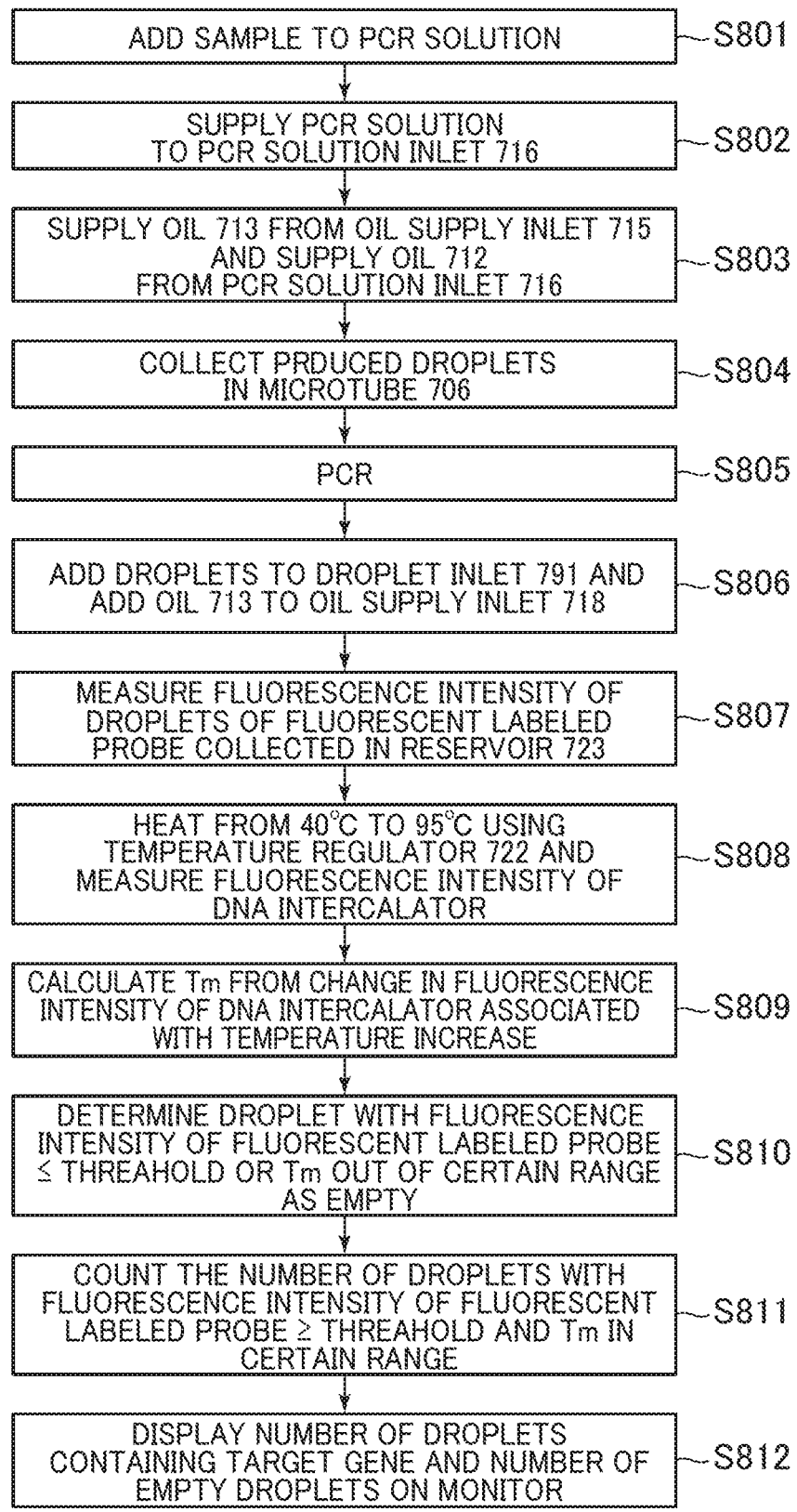
FIG. 8 shows a flowchart illustrating one embodiment of a method of measuring Tm using a DNA intercalator in the measurement in which the device and the cartridges in FIG. 7 are used.

An example of a method of measuring Tm using the device and the cartridges shown in FIG. 7 and an DNA intercalator is described with reference to the flowchart shown in FIG. 8. A sample containing DNA, which has been derived from a biological material, is added to a PCR solution containing DNA polymerase, primers, a fluorescent labeled probe, a DNA intercalator, deoxyribonucleotides, and buffer (S801). For the fluorescent labeled probe, a TaqMan probe that is hydrolyzed by DNA polymerase and emits fluorescence is used. The PCR solution is supplied to the PCR solution inlet 716 of the cartridge for droplet production 705 (S802). The cartridge 705 for droplet production is mounted onto the droplet production unit 701 of the PCR measurement device 721. When The oils 713 and 712 are supplied through the oil supply inlet 715 and the PCR solution inlet 716, respectively (S803), droplets are generated at an intersection where the flow path for the oil in the cartridge 705 for droplet production crosses the flow path for the PCR solution. The generated droplets are discharged through the droplet discharge outlet 717 and are transferred to the microtube 706 which has been installed in the thermal cycler in advance and collected in the tube (S804). When a desired number of droplets has been obtained, the lid of the microtube 706 is closed, and PCR is performed under the temperature control by the thermal cycler (S805). By repeating cycles consisting of steps of denaturation, extension, and annealing, DNA is amplified, and degradation of the fluorescent labeled probe occur in the extension step, resulting in an increase in fluorescence intensity. Reaction conditions such as the temperature and duration of each step and the number of cycles can easily be determined by a person skilled in the art. After PCR, when the temperature is decreased to the room temperature, synthesized DNA forms a double-strand with which the DNA intercalator intercalates to emit fluorescence. After the completion of the PCR, droplets and the oil 713 are added to the droplet inlet 719 and the oil supply inlet 718, respectively, of the cartridge for droplet detection which has been loaded on the droplet detection unit 703 in advance (S806). In the droplet detection unit 703, fluorescence intensities of the fluorescent labeled probes in the droplets collected in the reservoir 723 of the cartridge for droplet detection are measured (S807). The reservoir 723 of the cartridge for droplet detection is heated from 40° C. to 95° C. by using the temperature regulator 722 and the fluorescence intensity of the DNA intercalator is measured (S808). The detected fluorescence data is sent to the calculation unit (not shown) and the change in fluorescence intensity of the DNA intercalator caused by the temperature increase is differentiated with respect to change in temperature there, thereby a temperature at the inflection point on the fluorescence intensity curve is calculated as Tm (S809). A droplet with a fluorescence intensity of the fluorescent labeled probe being equal to or smaller than a threshold value and/or a droplet with Tm being out of a certain range are/is determined to be an empty droplet which does not contain the target gene (S810). The number of the droplets with a fluorescence intensity of the fluorescent labeled probe being equal to or larger than the threshold and the droplets with Tm falling in the certain range is counted (S811). The number of the droplets which contain the target gene and the number of the empty droplets are displayed on the monitor (S812). Note that the given threshold for a fluorescence intensity and a certain range for Tm can be determined in advance by an operator through, for example, pilot experiments.

The sample used is not limited as long as it contains target DNA, and examples thereof include biological samples such as body fluids and tissues, cells, and excrements of animals and plants, and samples containing fungi or bacteria such as soil samples. Examples of the body fluids include blood, saliva, and cerebrospinal fluid. Cell-free DNA (cfDNA) and circulating tumor DNA (ctDNA) present in blood are included. Examples of the tissues include a portion of an affected site obtained by surgery or biopsy (e.g., cancer tissues of breast or liver). The tissues may be fixed ones, such as formalin-fixed, paraffin-embedded (FFPE) tissue sections. Examples of the cells include those present at or around an affected site collected by biopsy and tumor cells circulating in the blood. These samples can be subjected to any pre-treatment. The samples after having been collected from a living body or an environment and homogenated in a suspension or dissolved with a solution for dissolution may be used as they are, but those obtained after extraction or purification of nucleic acids therein are preferably used.

Oil is a chemically inert substance which is insoluble or hardly soluble in the PCR solution constituting the droplets and is preferably a substance which is stable against temperature change in a high temperature range like in PCR. Fluorine-based oils, silicone-based oils, and hydrocarbon-based oils can be used. Examples of the fluorine-based oils include perfluorocarbon and hydrofluoroether. Fluorine-based oils having longer carbon chains are preferable because of their lower volatility. In addition, since fluorine-based oils have a specific gravity of greater than 1.7 and are denser than water with a specific gravity of 1 which serves as the solvent of the PCR solution, the produced droplets float on the oil. Examples of the silicone-based oils include polyphenylmethylsiloxane and trimethvlsiloxysilicate. Unlike the fluorine-based oils, silicone-based oils have a specific gravity of about 0.98 which is closer to that of water as the solvent of the PCR solution. Accordingly, the produced droplets are uniformly distributed in oil. Examples of the hydrocarbon-based oils include mineral oils, liquid paraffin, and hexadecane. Since the hydrocarbon-based oils have a specific gravity of about 0.84 and are less dense than water which serves as the solvent of the PCR solution, the produced droplets sink in the oil.

The oil may be used with the addition of a surfactant. The surfactant may be of any kind, but Tween 20, Tween 80, Span 80, and Triton X-100 can be used.

Figure 9:
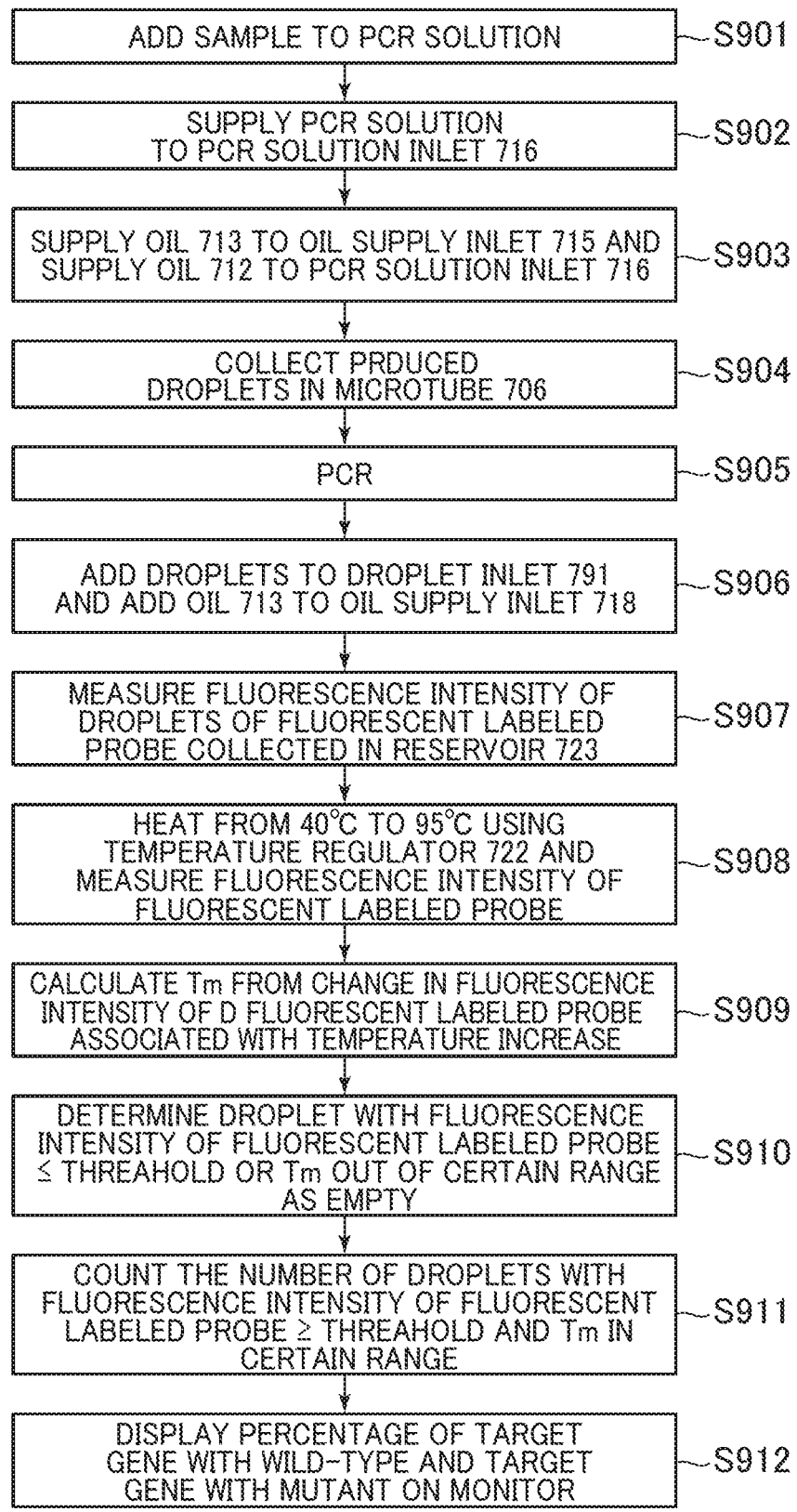
FIG. 9 shows a flowchart illustrating one embodiment of a method of measuring Tm using a fluorescent labeled probe in the measurement in which the device and the cartridges in FIG. 7 are used.

Next, an example of a method of measuring Tm using a fluorescent labeled probe such as a molecular beacon in place of the DNA intercalator is described with reference to the flowchart shown in FIG. 9. A sample containing DNA, which has been derived from a biological material, is added to a PCR solution containing DNA polymerase, primers, a fluorescent labeled probe, deoxyribonucleotides, and pH buffer (S901). For the fluorescent labeled probe, for example, a molecular beacon can be used, which forms a stem-loop structure when it is present in a free form and emits fluorescence when it anneals to the template DNA, causing the fluorescent dye and the quencher to separate from each other. The PCR solution in the cartridge 705 for droplet production is supplied to the PCR solution inlet 716 (S902). The cartridge 705 for droplet production is mounted onto the droplet production unit 701 of the PCR measurement device 721. The oils 713 and 712 are supplied to the oil supply inlet 715 and the PCR solution inlet 716, respectively (S903). Droplets are generated at an intersection where the flow path for the oil in the cartridge 705 for droplet production crosses the flow path for the PCR solution. The produced droplets are discharged through the droplet discharge outlet 717 and are transferred to and collected in the microtube 706 which has been installed in the thermal cycler in advance (S904). When a desired number of droplets has been obtained, the lid of the microtube 706 is closed, and PCR is performed under the temperature control by the thermal cycler (S905). By repeating cycles consisting of steps of denaturation, extension, and annealing, DNA is amplified in the extension step and more fluorescent labeled probes anneal to DNA, separating the fluorescent dye from the quencher, resulting in an increase in fluorescence intensity. Reaction conditions such as the temperature and duration of each step and the number of cycles can easily be determined by a person skilled in the art. After the completion of the PCR, droplets and the oil 713 are added to the droplet inlet 719 and the oil supply inlet 718, respectively, of the cartridge for droplet detection which has been loaded on the droplet detection unit 703 in advance (S906). In the droplet detection unit 703, fluorescence intensities of the fluorescent labeled probes in the droplets collected in the reservoir 723 of the cartridge for droplet detection are measured (S907). The reservoir 723 of the cartridge for droplet detection is heated from 40° C. to 95° C. using the temperature regulator 722 and the fluorescence intensity of the fluorescent labeled probe is measured (S908). The measured fluorescence data is sent to the calculation unit; the change in fluorescence intensity of the fluorescent labeled probe associated with the temperature increase is differentiated with respect to change in temperature there; and a temperature at the inflection point on the fluorescence intensity curve is calculated as Tm (S909). Droplets with a fluorescence intensity of the fluorescent labeled probe being equal to or smaller than a threshold and/or a droplet with Tm being out of a certain range are determined to be empty droplets which do not contain the target gene (S910). The number of the droplets with a fluorescence intensity of the fluorescent labeled probe being equal to or larger than the threshold and the droplets with Tm falling in the certain range is counted (S911). The number of the droplets which contain the target gene and the number of the empty droplets are displayed on the monitor (S912). Note that a certain threshold for the fluorescence intensity and a range for a certain Tm can be determined in advance by an operator through, for example, pilot experiments.

FIGS. 10 and 11 each shows one example of a representation of a measurement result displayed on the monitor. The number of droplets that has been counted for each kind of cancer-related genes or each kind of mutations may be displayed as shown in FIG. 10, or the percentage of droplets that has been counted for each kind of cancer-related genets or each kind of mutations may be displayed as shown in FIG. 11. The results displayed on the monitor may include, in addition to the number or percentage of droplets as shown in FIG. 10 or 11, respectively, a graph obtained by plotting measurements for droplets with three axes, i.e., the green fluorescence intensity, the yellow fluorescence intensity and Tm as shown in the lower panel in FIG. 1. Furthermore, a histogram obtained by plotting the number of droplets relative to the fluorescence intensity of the fluorescent labeled probe or Tm may also be included. With such graph and/or histogram in sight, a user can change the settings of the threshold value for the fluorescence intensity of the fluorescent labeled probe and/or the range for Tm and again perform counting of the number of droplets of which fluorescence intensity meeting the threshold criteria and/or Tm falling in a given range.

(3) Program

An embodiment of the present invention is a program for causing a DNA detection device to perform a DNA detection method. The DNA detection device used here is the device described in detail in the section (2) and the method described in detail in the section (1) is performed as the DNA detection method.

EXAMPLE

In this example, results obtained by measuring Tm of DNA in droplets using a DNA intercalator are described.

First, double-stranded DNA of 16, 23, and 78 bp in length were prepared. Next, they were mixed with a buffer in the final concentration of 0.2 µM, 0.4 µM, or 0.8 µM, respectively. The buffer was prepared to contain a salt such as potassium chloride or magnesium chloride, and a fluorescent labeled probe or the DNA intercalator (e.g., a double-stranded DNA binding dye such as EvaGreen®) as the DNA intercalator.

By using these reaction solutions and a fluorine-based oil containing a surfactant, droplets of 20 µm in diameter were produced through a microchannel. The produced droplets were enclosed in flat capillary tubes of 0.1 mm in height and 1 mm in width. The tubes were placed on a temperature regulation stage and change in fluorescence intensity of each single droplet subjected to elevated temperatures was observed under a microscope.

FIG. 12A shows a graph showing change in fluorescence intensities, in association with the temperature increase, of the droplets which contain the double-stranded DNA of 23 bp and a fluorescent labeled probe or the DNA intercalator (e.g., a double-stranded DNA binding dye such as EvaGreen®). The fluorescence intensities of the droplets decreased as the temperature increased. FIG. 12B shows a graph produced by plotting temperature as the abscissa and negative first-order derivative of the fluorescence intensity as the ordinate, based on the results shown in FIG. 12A, and the maximum value is defined as a Tm value. The results of measurement of Tm in the droplets which contain the double-stranded DNA of different lengths at different concentrations and in a bulk are arranged in Table 1.

TABLE 1

|  | 16 bp | 23 bp | | | 78 bp |
|---|---|---|---|---|---|
|  | 0.4 µM | 0.2 µM | 0.4 µM | 0.8 µM | 0.4 µM |
| Droplet | 54° C. | 58° C. | 58° C. | 59° C. | 74° C. |
| Bulk | 57° C. | 63° C. | 64° C. | 64° C. | 80° C. |

As can be seen from Table 1, the results of measurement of Tm in the droplets and the bulk correspond well to each other, i.e., the Tm values becomes higher as the DNA becomes longer and substantially constant even if concentrations of DNA are different.

As described above, it is possible to determine the identity of DNA contained in each droplet by measuring Tm, even for empty droplets which do not contain the target gene and droplets in which the reaction efficiency of the PCR is insufficient. Accordingly, the measurement reproducibility and measurement accuracy can be improved by measuring Tm of the PCR amplification product in addition to the color and the fluorescence intensity of the fluorescent labeled probe to discriminate empty droplets which do not contain the target gene and droplets in which the reaction efficiency of the PCR is insufficient with the measurement device and correcting the data to be analyzed according to the measurement results.

INDUSTRIAL APPLICABILITY

The present invention made it possible to provide novel PCR measuring methods and measurement devices using droplets.

Denotation of symbols
- 101 droplet which contains a gene with the wild-type allele
- 102 droplet which contains a gene with the mutant A allele
- 103 droplet which contains a gene with the mutant B allele
- 104 empty droplet
- 201 droplet which contains a gene with the wild-type allele
- 202 droplet which contains a gene with the mutant A allele
- 203 droplet which contains a gene with the mutant B allele
- 204 empty droplet
- 301 droplet which contains the target gene
- 302 droplet which does not contain the target gene
- 303 microchannel
- 304 light source
- 305 filter
- 306 photo-multiple meter
- 307 CCD
- 308 lens
- 309 dichroic mirror
- 310 cartridge for droplet detection
- 311 droplet
- 312 temperature regulator
- 401 droplet which contains a gene with the wild-type allele 402 droplet which contains a gene with the mutant A allele
403 droplet which contains a gene with the mutant B allele
404 empty droplet
405 droplet a
406 droplet b
407 droplet c
501 DNA
502 DNA intercalator
503 Tm
601 DNA
602 fluorescent labeled probe
603 fluorescent dye
604 quencher
605 Tm
701 droplet production unit
702 thermal cycler
703 droplet detection unit
704 monitor
705 cartridge for droplet production
706 microtube
707 cartridge for droplet detection
708 to 711 pumps
712 oil
713 oil
714 waste liquid reservoir
715 oil supply inlet
716 PCR solution inlet
717 droplet discharge outlet
718 oil supply inlet
719 droplet inlet
720 waste liquid discharge outlet
721 PCR measurement device
722 temperature regulator
723 reservoir
724 control unit

The invention claimed is:

1. A method for determining whether or not each of a plurality of target DNAs is contained in each of a plurality of droplets in oil, each droplet containing a plurality of fluorescent labeled probes, each fluorescent labeled probe comprising a fluorescent dye and a quencher conjugated at or in a vicinity of respective ends thereof being hybridized to a corresponding target DNA of the plurality of target DNAs between the fluorescent dye and the quencher, and being configured to form a stem-loop structure by sequences near both ends, the sequences being complementary to each other, the plurality of fluorescent labeled probes comprises at least a first fluorescent labeled probe and a second fluorescent labeled probe, wherein the first and second fluorescent labeled probes each comprise a first fluorescent dye associated with a first fluorescence color, wherein the first fluorescent labeled probe is configured for hybridization to a first target DNA and the second fluorescent labeled probe is configured for hybridization to a second target DNA of the plurality of target DNAs that is different from the first target DNA, the method comprising:
 a first step of performing a nucleic acid amplification reaction in the plurality of droplets;
 a second step of, after completion of the nucleic acid amplification reaction, measuring fluorescence intensity associated with the plurality of fluorescent labeled probes in each droplet of the plurality of droplets at a plurality of increasing temperatures, wherein the fluorescence intensity associated with the plurality of fluorescent labeled probes comprises a fluorescence intensity associated with the first fluorescence color;
 a third step of calculating, for each droplet in the plurality of droplets with a measured fluorescence intensity above a threshold fluorescence intensity, at least one melting temperature (Tm) associated with at least one fluorescent labeled probe of the plurality of fluorescent labeled probes in the droplet by identifying at least one corresponding inflection point of the measured fluorescence intensity of the at least one fluorescent labeled probe;
 a fourth step of determining,
  that the first target DNA is not contained in droplets in a first set of droplets in the plurality of droplets based on (1) the measured fluorescence intensity being below the threshold fluorescence intensity or (2) the measured fluorescence intensity being above the threshold fluorescence intensity and a first calculated Tm of the at least one calculated Tm being out of a first predetermined range of Tm around a first reference Tm calculated for the first fluorescent labeled probe of the at least one fluorescent labeled probe and the first target DNA of the plurality of target DNAs in bulk, and
  that the second target DNA is not contained in droplets in a second set of droplets in the plurality of droplets based on (1) the measured fluorescence intensity being below the threshold fluorescence intensity or (2) the measured fluorescence intensity being above the threshold fluorescence intensity and a second calculated Tm of the at least one calculated Tm being out of a second predetermined range of Tm around a second reference Tm calculated for the second fluorescent labeled probe of the at least one fluorescent labeled probe and the second target DNA of the plurality of target DNAs in bulk, wherein the first reference Tm is different from the second reference Tm;
 a fifth step of counting:
  a first number of droplets in a third set of droplets in the plurality of droplets, wherein the third set of droplets are determined to contain the first target DNA based on (1) the measured fluorescence intensity being equal to, or larger than, the threshold fluorescence intensity and (2) the first calculated Tm being in the first predetermined range of Tm around the first reference Tm, and
  a second number of droplets in a fourth set of droplets in the plurality of droplets, wherein the fourth set of droplets are determined to contain the second target DNA based on (1) the measured fluorescence intensity being equal to, or larger than, the threshold fluorescence intensity and (2) the second calculated Tm being in the second predetermined range of Tm around the second reference Tm; and
 a sixth step of displaying, on a monitor, a set of values related to (1) a third number of droplets in an intersection of the first set of droplets and the second set of droplets that do not contain at least one of the first target DNA and the second target DNA, (2) the first number of droplets in the third set of droplets that contain the first target DNA, and (3) the second number of droplets in the fourth set of droplets that contain the second target DNA.

2. The method according to claim 1, wherein the plurality of droplets are planarly disposed.

3. The method according to claim 1, wherein the oil comprises a fluorine-based oil, a silicone-based oil, or a hydrocarbon-based oil.

4. The method of claim 1, wherein the first predetermined range of Tm is selected to include a first Tm associated with the first fluorescent labeled probe hybridized with the first target DNA and to exclude a Tm associated with the first fluorescent labeled probe in the absence of the first target DNA.

5. The method of claim 1, wherein the first target DNA is a first mutation of a wild type target DNA and the second target DNA is a second mutation of the wild type target DNA.

6. The method of claim 5, wherein the plurality of fluorescent labeled probes further comprises a third fluorescent labeled probe comprises a second fluorescent dye associated with a second fluorescence color and the fluorescence intensity associated with the plurality of fluorescent labeled probes further comprises a second fluorescence intensity associated with the second fluorescence color, wherein the third fluorescent labeled probe is configured for hybridization to a wild type target DNA, wherein the first reference Tm and the second reference Tm are different from a third reference Tm calculated for the third fluorescent labeled probe and the wild type target DNA of the plurality of target DNAs in bulk, and wherein:

the fourth step further comprises determining,
that the wild type target DNA is not contained in droplets in a fifth set of droplets in the plurality of droplets based on (1) the measured second fluorescence intensity associated with the second fluorescence color being below a second threshold fluorescence intensity associated with the second fluorescence color or (2) the measured second fluorescence intensity being above the second threshold fluorescence intensity and a third calculated Tm of the at least one calculated Tm being out of a third predetermined range of Tm around the third reference Tm;

the fifth step further comprises counting:
a fourth number of droplets in a sixth set of droplets in the plurality of droplets, wherein the sixth set of droplets are determined to contain the wild type target DNA based on (1) the measured second fluorescence intensity being equal to, or larger than, the second threshold fluorescence intensity and (2) the third calculated Tm being in the third predetermined range of Tm around the third reference Tm; and the sixth step further comprises displaying, on the monitor, the fourth number of droplets in the sixth set of droplets that contain the wild type target DNA, wherein the third number of droplets is a third number of droplets in the intersection of the first set of droplets, the second set of droplets, and the fifth set of droplets that do not contain at least one of the first target DNA, the second target DNA, or the wild type target DNA.

7. The method of claim 6, wherein displaying the set of values comprises displaying, on the monitor, (1) a first percentage of droplets containing the first target DNA, (2) a second percentage of droplets containing the second target DNA, (3) a third percentage of droplets containing the wild type target DNA, and (4) a fourth percentage of droplets not containing the first target DNA, the second target DNA, or the wild type target DNA.

8. The method of claim 6, wherein the counting the first number of droplets in the third set of droplets and counting the second number of droplets in the fourth set of droplets is further based on the measured fluorescence intensity being associated with the first fluorescence color, and counting the fourth number of droplets in the sixth set of droplets is further based on the measured fluorescence intensity being associated with the second fluorescence color.

9. The method of claim 8, wherein the plurality of droplets contain different amounts of the first fluorescent labeled probe and the second fluorescent labeled probe in a known ratio such that, for a particular droplet, a particular measured fluorescence intensity of the first fluorescence color above an additional threshold fluorescence intensity indicates that the particular droplet contains the first target DNA.

10. The method of claim 1, wherein the second predetermined range of Tm around a second reference is non-overlapping with the first predetermined range of Tm around a first reference.

* * * * *